US009646804B2

(12) United States Patent
Foucher et al.

(10) Patent No.: US 9,646,804 B2
(45) Date of Patent: May 9, 2017

(54) METHOD FOR CALIBRATION OF A CD-SEM CHARACTERISATION TECHNIQUE

(71) Applicant: COMMISSARIAT À L'ÉNERGIE ATOMIQUE ET AUX ÉNERGIES ALTERNATIVES, Paris (FR)

(72) Inventors: Johann Foucher, Voreppe (FR); Jérôme Hazart, Eybens (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/913,448

(22) PCT Filed: Aug. 7, 2014

(86) PCT No.: PCT/FR2014/052060
§ 371 (c)(1),
(2) Date: Feb. 22, 2016

(87) PCT Pub. No.: WO2015/025098
PCT Pub. Date: Feb. 26, 2015

(65) Prior Publication Data
US 2016/0203945 A1    Jul. 14, 2016

(30) Foreign Application Priority Data

Aug. 21, 2013  (FR) ...................................... 13 58108

(51) Int. Cl.
*G01D 18/00* (2006.01)
*H01J 37/28* (2006.01)
(Continued)

(52) U.S. Cl.
CPC .......... *H01J 37/28* (2013.01); *G01N 23/2251* (2013.01); *G03F 7/70516* (2013.01);
(Continued)

(58) Field of Classification Search
CPC .. G01B 21/042; G01D 18/00; G03F 7/70516; G03F 7/7011
See application file for complete search history.

(56) References Cited

U.S. PATENT DOCUMENTS

2005/0197772 A1* 9/2005 Archie ................. G01B 21/045
702/1
2008/0319696 A1   12/2008 Tanaka et al.

OTHER PUBLICATIONS

H. Marchman, "Scanning electron microscope matching and calibration for dimensional metrology," 1998, Microelectronic Engineering, vol. 41/42, pp. 597-602.*

(Continued)

*Primary Examiner* — Kiho Kim
(74) *Attorney, Agent, or Firm* — Pillsbury Winthrop Shaw Pittman LLP

(57) ABSTRACT

A calibration method for a CD-SEM technique, includes determining a match function converting at least one parameter obtained by modelling a measurement supplied by the CD-SEM technique into a function of at least one parameter representative of a measurement supplied by a characterisation technique different from the CD-SEM technique, the match function being characterised by a plurality of coefficients; performing measurements on a plurality of patterns chosen to cover the desired validity range for the calibration, the measurements being done using both the CD-SEM technique to be calibrated and the reference technique; determining, from the measurements, a set of coefficients of the match function minimising the distance between the functions of the parameters measured using the reference technique and applying the match function to the parameters obtained by modelling measurements supplied by the CD-SEM; using the set of coefficients during the implementation of the calibrated CD-SEM technique.

9 Claims, 4 Drawing Sheets

(51) Int. Cl.
G03F 7/20 (2006.01)
G01N 23/225 (2006.01)
H01J 37/26 (2006.01)

(52) U.S. Cl.
CPC ........ *G03F 7/70625* (2013.01); *H01J 37/265* (2013.01); *G01B 2210/56* (2013.01); *H01J 2237/28* (2013.01); *H01J 2237/2826* (2013.01)

(56) References Cited

OTHER PUBLICATIONS

Cresswell et al., "Comparison of SEM and HRTEM CD measurements extracted from test-structures haying feature linewidths from 40 nm to 240 nm," Apr. 2005, Proceedings of IEEE 2005 International Conference on Microelectronic Test Structures, vol. 18 pp. 11-16.*

International Search Report as issued in International Patent Application No. PCT/FR2014/052060, dated Jan. 7, 2015.

Li, Y.G., et al., "Monte Carlo Simulation of CD-SEM Images for Linewidth and Critical Dimension Metrology," Scanning vol. 35, 2013, pp. 127-139.

Frase, C.G., et al., "CD characterization of nanostructures in SEM metrology," Institute of Physics Publishing, Meas. Sci. Technol. 18, 2007, pp. 510-519.

Orji, N.G., et al., "A Systematic Approach to Accurate Evaluation of CD-Metrology Tools," 2007 IEEE International Conference on Microelectronic Test Structures, 5 pages.

Foucher, J., et al., "Hybrid Metrology for Critical Dimension based on Scanning Methods for IC Manufacturing," Proceedings of SPIE, vol. 8378, 2012, pp. 83780F-83780F-8.

* cited by examiner

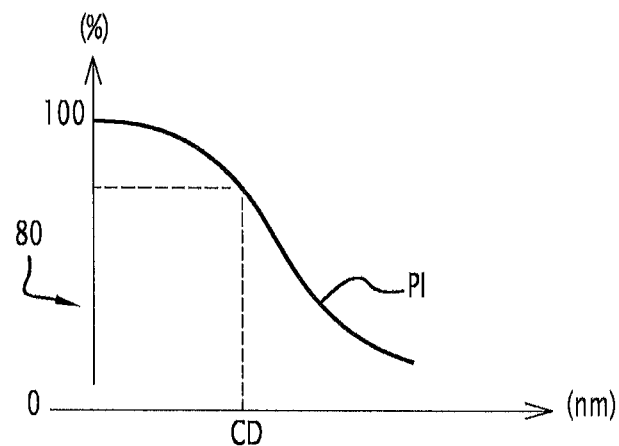
FIG.1
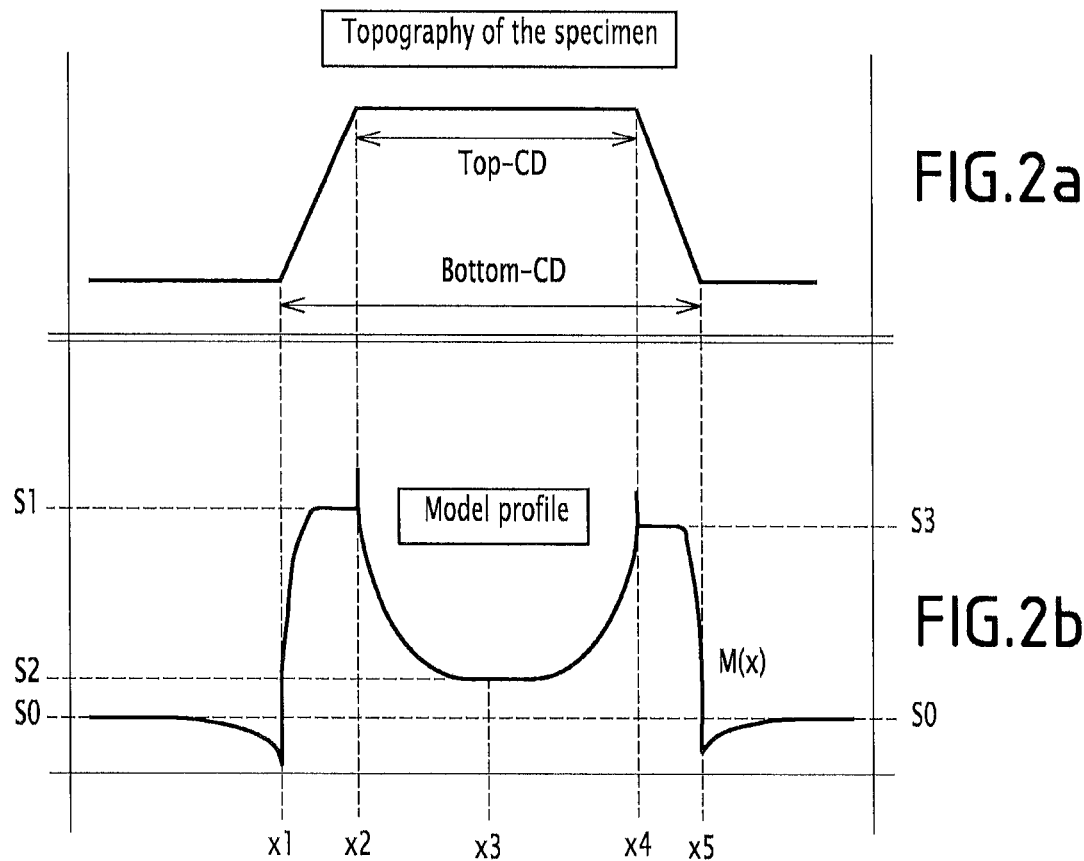
FIG.2a
FIG.2b

METHOD FOR CALIBRATION OF A CD-SEM CHARACTERISATION TECHNIQUE

CROSS-REFERENCE TO RELATED APPLICATIONS

This is the U.S. National Stage of PCT/FR2014/052060, filed Aug. 7, 2014, which in turn claims priority to French Patent Application No. 1358108, filed Aug. 21, 2013, the entire contents of all applications are incorporated herein by reference in their entireties.

The present invention relates to the field of metrology and its object is a method for calibrating a technique of characterisation by scanning electron microscopy to determine a critical dimension, called the CD-SEM technique. The method according to the invention is, more specifically, able to characterise the patterns used in microelectronic integrated circuits obtained in the microelectronics industry.

In microelectronics progress of the technology goes hand-in-hand with requirements for characterisation instruments. With each new technology node the metrology tools must be more advanced in order to check the dimensions of the manufactured devices.

Various techniques for characterising the dimensions of manufactured objects are known; these include, non-exhaustively: Scanning Electron Microscopy (SEM), Atomic Force Microscopy (AFM), Optical Critical Dimension (OCD) and Transmission Electron Microscopy (TEM).

Atomic Force Microscopy, AFM, is a technique of microscopy by scanning of a mechanical probe, which was developed in the ninety-eighties and afterwards, and which enables a resolution at a nanometric scale to be obtained. The essential component of a conventional atomic force microscope is a probe consisting of a lever connected to a bracket end fitted, at the opposite end, with a point directed towards the surface or object to be observed. The lever is generally some tens or hundreds of micrometres long, and the point generally has a radius of curvature of several tens of nanometres or less. This very fine point moves in very close proximity to the object (of the order of one nanometre, or less), whilst oscillating. Under the effect of the Van Der Waals forces the mechanical properties of the point are modified, in particular, the amplitudes, phases and resonance frequency of the point's oscillations. By measuring these variations the position of the object relative to the point can be known. The point is simultaneously scanned very precisely in proximity to (or in contact with) the sample. By this means, if the position of the point and the proximity of the object are known, the topography of the object can be deduced. AFM measurements, enable the profiles of the patterns to be measured. In particular, the information is described by a set of points or functions of the type $z_i = f(x_i)$ or $z = f(x)$, where z is the altitude of the profile as a function of lateral coordinate x. A general extension to three dimensions is obtained directly by adding a second lateral coordinate.

One of the problems of AFM technology which is posed is that of the complete characterisation (shapes and dimensions) of the point used. This step of characterisation is fundamental for the accuracy and reproducibility of the measurements. The AFM data can thus be corrupted by lack of knowledge of the shape of the AFM point, or of the physical interactions between the point and the materials in question (the Van der Waals forces are dependent on the materials in question). Secondly, the measured objects can be rough, and it is possible that this roughness may not be taken into account by the AFM technology, due to the resolution of the mechanical movements of the point's micro-positioners, or alternatively the minimum radius of curvature of the point in question. Finally, certain portions of the profile may not be obtained precisely, due to the mechanical encumbrance of the points used. In addition, the measuring time may be too long for regular use in checking manufacturing methods.

OCD (Optical Critical Dimension) scatterometry is an optical technique which allows measurement of a pattern profile (usually repeated periodically on a structure with a plurality of identical patterns positioned periodically, so as to obtain more information), through an analysis of the optical response of the object in question to a controlled light excitation (controlled in terms of wavelength, polarisation, angle of incidence, etc.). The nature of the measured optical response may vary greatly, and may be the intensity, phase or phase difference between the polarisations, depending on the angles of incidence, the wavelengths or the excitation polarisations. It requires that, in a first step, a geometrical model is defined together with models for the refractive index laws of the materials. The geometry and/or the index laws of the materials are configured by a set of parameters (fixed or variable). For a given set of parameters a theoretical response of the object to a given light excitation is calculated. This theoretical response is fitted to the experimental response measured by the scatterometer by modifying the values of the parameters. The difference between the experimental response and the theoretical response can be minimised by adjusting the real and imaginary parts of the optical index in order to make the difference between the experimental response and the theoretical response less than or equal to a given threshold, or until it is no longer possible to reduce the difference between theory and experiment by varying the parameters below a certain variation threshold. An example of a minimisation method is the libraries method, which enables the reverse problem to be resolved (if the direct problem is defined as the calculation of a scatterometric signature from a set of parameters, the reverse problem then consists in finding the set of parameters from the measurement of the scatterometric signature). The libraries method consists in pre-calculating, for a number of vectors of parameters, the theoretical optical responses (signatures), and then in seeking to determine the vector of parameters for which the experimental signatures and the pre-calculated signatures of the library (or a combination of these signatures) fit one another. Thus, in a production context, the measurement time is not constrained by the signatures' calculation times (since they are already stored in the library), but by the time spent searching for the best signature(s) in the library. In many cases, the parameters obtained are then refined by a process of iterative calculation to obtain improved accuracy (where the accuracy of the library generally relates to the parameters' sampling resolution). When the fit is optimal the configured values found are considered to be measurements. There are many types of scatterometers: they include, for example, scatterometers based on ellipsometry (multi- or mono-wavelength, possibly multi-angle), reflectometry (with control of polarisation), photogoniometry (variable angle, with one or more wavelengths, with variable polarisation), microscopy, etc., or combinations of these various configurations. Scatterometry is, however, subject to many measurement artifacts, such as the inaccuracy of the chosen geometrical model, and of the chosen materials models, roughness effects which are not taken into account, noise of the detectors, imperfections of the optical components and their alignment, etc. In addition, resolution of the reverse scatterometric problem leads to an estimate of the geometrical and/or materials parameters, which are correlated with one another, adding an additional inaccuracy.

Transmission Electron Microscopy, TEM, is a reference imaging technique where a beam of high-energy electrons is passed through a fine section of an object/material which it is desired to characterise. The contrast of the image is principally due to the contrast of the atomic numbers of the elements comprising the object. The accuracy of this technique is at the atomic level. This technique is very accomplished in the world of microelectronics, and is used on a daily basis by research and development teams. In particular it enables the morphology of the objects to be obtained, gives indications concerning doping levels, and provides an absolute metrological reference. TEM technology does, however, have certain limitations, including:

- a long time to prepare samples (currently 4 hours);
- samples containing organic elements may damaged;
- it is a destructive technique, since the patterns on the wafers are cut in order that they can be seen by the slice;
- as with AFM, the measurement is very accurate but very local, and the time required to prepare the samples means that it is difficult to conceive of systematic measurement on a wafer in the current state of the technology.

The SEM technique consists in directing a very fine beam of electrons (called primary electrons) towards a point of the sample, and in obtaining the electrons generated by this excitation (secondary electrons), by electrodes positioned close to the sample. A stream of secondary electrons is thus produced for each point. Since the beam scans the entire sample point-by-point, an image of secondary electrons is formed. There several ways of using the SEM technique, depending on the applications and information which it is desired to obtain from the images. The semiconductor industry thus defines and monitors the dimensions of the manufactured products using what is called the CD, or Critical Dimension. In this context the CD-SEM version (Critical Dimension-Scanning Electron Microscope) of SEM technology is very widely used. The beam is projected on to the surface of the sample at an angle of incidence which is generally perpendicular to the surface of the wafer. The image obtained is a grey-level image, and the geometrical measurements of the objects are determined by an analysis of the contours of the objects obtained after one or more threshold(s) is/are chosen. In certain microscopes the images are obtained with oblique incident beams, in order that one or more image(s) of the objects are produced, seen from the side. It is possible, for example, to reconstruct a graph as illustrated in FIG. 1 representing a profile of intensity of secondary electrons PT with, along the ordinate, a percentage of secondary electrons obtained and, along the abscissa, a dimension, measured in nm, representing the scanning position. But one of the major problems is the interpretation of the images by thresholding algorithms: the choice of this threshold will, indeed, determine the value of the CD sought. It is currently considered, often wrongly, that a threshold of secondary electrons obtained empirically, for example of 80%, is applicable to all types of pattern. The 80% threshold is therefore applied, and used to deduce the measured critical dimension, whatever the type of pattern analysed. But the choice of threshold is often arbitrary, and the optimum choice is different for each object, in particular depending on the height of the patterns, the materials involved, the dimensions of the objects, the pattern density, etc. It is currently known that CD-SEMs give poor measurements for objects smaller than 100 nm (difference from reality between one nanometre and several nanometres). An empirical fixed threshold applied to all types of pattern is even less satisfactory since there is no direct physical relationship between the percentage of secondary electrons obtained and the actual height of the pattern the critical dimension of which it is sought to determine.

In other words, although a measurement using 80% of secondary electrons is made, this does not however mean that a critical dimension at 80% of the height of the pattern is measured.

Two known approaches are envisaged to resolve the problem of dimension determination depending strongly on an empirically defined threshold providing no robust solution (false or unstable measurements). The first solution consists in producing a complete physical model of the image. This solution as described in particular in the article "Monte Carlo Simulation of CD-SEM Images for Line width and Critical Dimension Metrology" (Y. G. Li, P. Zhang, and Z. J. Ding, Scanning, August 2012). The path and response of the patterns and materials are modelled on physical bases by techniques of the Monte Carlo type. The rate of secondary electrons is calculated for each position of the beam of primary electrons. The main advantage lies in the fact that, in principle, the physical modelling of the interaction of a pattern with an electron beam enables a very large variety of cases to be processed with a minimum of physical parameters. But this minimum of parameters is very large since it takes account:

- of the formation lens of the electron beam (width of the beam), of the detectors of the secondary electrons (or primary electrons, in certain cases) and of the electron charge effects;
- of the nature of the materials (average free path of the primary and secondary electrons, nuclear charge, density, etc.) and their organisation (for example, into sub-layers);
- of the topography or geometry of the patterns to be measured (inclination, corners, etc.).

In practice these parameters are very difficult to measure and the experiments to determine them are long and complex, or sometimes impossible. Approximations must therefore be made, and the rendering of the images is valid only in a very small number of cases. In addition, the calculation time is very long and does not lend itself to processing a large number of images. The second solution consists of making a parametric mathematical model of the images; such a solution is described, in particular, in the article "CD characterization of nanostructures in SEM metrology" (C. G. Frase, E. Buhr, and K. Dirscherl, Meas. Sci. Technol., vol. 18, n° 2, p. 510, February. 2007). Parametric mathematical functions (i.e. functions the shape and amplitude of which are determined by the value of parameters) are chosen to represent optimally the SEM images of the reference samples. These functions can be chosen according to a simple phenomenological model, or alternatively by an analysis of preliminary Monte Carlo models describing the formation of the SEM images (more complex and precise, but requiring longer calculation times). An example of such M(x) functions is illustrated in FIG. 2b for a pattern having a trapezoid shape represented in FIG. 2a. According to this example, the pattern is broken down into horizontal sections (in this case, six sections), where each section corresponds to a particular shape function. The M(x) function can therefore be broken down as follows (into six functions for each of the sections):

$$M(x) := \begin{cases} S0 + Ae^{\frac{x-x1}{t0}} & x < x1 \\ S1 - (S1 - S0 - A)e^{-\frac{x-x1}{t1}} & x1 \leq x \leq x2 \\ S2 + Ce^{-\frac{x-x2}{t2}} & x2 < x \leq x3 \\ S2 + De^{\frac{x-x4}{t3}} & x3 < x < x4 \\ S3 - (S3 - S0 - B)e^{\frac{x-x5}{t4}} & x4 \leq x \leq x5 \\ S0 + Be^{\frac{x5-x}{t5}} & x > x5 \end{cases}$$

The model shown above therefore includes plurality of variables: $x_1$, $x_2$, $x_3$, $x_4$, $x_5$, $S_0$, $S_1$, $S_2$, $S_3$, $t_0$, $t_1$, $t_2$, $t_3$, $t_4$, $t_5$, A, B, C, D, where the most interesting are those relative to the lateral dimensions of the pattern, i.e.: $x_1$, $x_2$, $x_4$ and $x_5$,.

More simple or more complex models can be produced depending on the type of sample, the quality of the images, or the pre-established information on the materials or profiles.

When the modelling is completed it is necessary, as in the case of scatterometry, to resolve a problem in reverse, i.e. by fitting the experimental data to the model by varying the parameters. The problem with these mathematical modelling techniques lies in the fact that, even if the basic modelling functions use simple physical bases, it is not known in reality how the parameters of the mathematical functions are connected to the real physical parameters, due to the simplification of the mathematical functions.

In this context, the aim of the present invention is to provide a method enabling the parameters derived from the physical or mathematical models obtained by measurements of a technique of characterisation by scanning electron microscopy to determine a CD-SEM critical dimension to be used more effectively and more accurately. The method according to the invention is a method for calibrating a parametric CD-SEM technique.

To this end the invention proposes a method of calibrating a technique of characterisation by scanning electron microscopy in order to determine a critical dimension, called a CD-SEM technique, where the said method includes the following steps:
  determination of a mapping function transforming at least one parameter obtained by modelling a measurement provided by the CD-SEM technique into a function of at least one parameter representative of a measurement provided by a reference characterisation technique different from the CD-SEM technique, where the said mapping function is characterised by a plurality of coefficients;
  making of measurements on a plurality of patterns chosen to cover the field of validity desired for the calibration, where the said measurements are produced using both the CD-SEM technique requiring calibration, and the reference technique;
  determination, from the said measurements, of a set of coefficients of the mapping function minimising the distance between the functions of the parameters measured by the reference technique and the application of the mapping function to the parameters obtained by modelling the measurements provided by the CD-SEM technique;
  use of the said set of coefficients when using the calibrated CD-SEM technique.

The term "critical dimension" is understood to mean the critical dimension(s) of a pattern representing one or more characteristic lengths of the pattern which are critical either for control of the manufacturing process, or to guarantee the electrical performance of the final electronic device consisting of the said patterns.

Generally speaking the invention consists in calibrating a parametric CD-SEM technique (i.e. a technique in which a mathematical or physical model of the CD-SEM image is made) by a richer reference technique, of the AFM, TEM or OCD type. The calibration consists in finding the coefficients of a mapping relationship (model) between the physical parameters determined by AFM, TEM or OCD and the modelling parameters found by the CD-SEM technique. It will be noted that, according to the invention, the calculation threshold of the CD of the CD-SEM technique, which is known often to be arbitrary, and which does not represent the geometrical reality of the pattern, is not modified.

More accurately, by virtue of the invention, an auxiliary reference characterisation technique (for example the AFM, TEM or OCD techniques) is advantageously used, relating the mathematical parameter(s) obtained from the CD-SEM measurements to one or more physical parameter(s) of interest obtained from the reference technique. When this mapping has been established between the mathematical parameter(s) and the physical parameter(s) of interest, a calibration of the CD-SEM technique is obtained, and the mapping function can then be used both in research and development, and in production; this mapping function enables a more accurate and more realistic value of the parameters sought to be obtained within the range of validity for which the samples were selected to accomplish the calibration.

The method according to the invention is based on the calibration of mathematical or physical models of CD-SEM data, firstly, and of data from the reference technique, secondly. The model used in the method according to the invention is preferably a mathematical model, since physical modelling remains a technique requiring very long calculation times.

The advantage of using a reference technique, for example OCD scatterometry, different to the CD-SEM technique, is illustrated in particular in FIGS. 3a and 3b. CD-SEM and OCD technologies are complementary from several standpoints. CD-SEM technology is an imaged technique, and a visual inspection enables the shapes of the objects requiring measurement to be determined at least coarsely. The analysis of the image with a view to obtaining accurate dimensions from it is, for its part, dependent on the geometry. OCD technology presupposes that a relatively accurate idea of the shapes of the object is already present, since it is a geometrical model which will then be optimised using the data derived from the OCD measurements. Pre-established information is therefore necessary, unlike with CD-SEM technology. However, OCD technology gives very great repeatability and accuracy. If the case of profiles of two different patterns are considered, one of them "narrowing" (FIG. 3b) and the other "expanding" (FIG. 3a), the CD-SEM technique can give ambiguous data; indeed, intensity profiles 1A (FIGS. 3a) and 1B (FIG. 3b) of the obtained secondary electrons are very similar, even though the geometry of the patterns is very different. It can easily be understood that an approach based solely on CD at an 80% threshold would be completely insufficient to reflect the reality, since a CD would be obtained which was almost identical for two patterns with different geometries. CD-SEM technology gives a certain level of information on the actual value of the lateral dimension of the profile (dimension w between each peak, or a function of w at a lower threshold), but loses the precise information on the angle of inclination and the lateral dimension. It can be noted that this information is already partially contained in the CD-SEM measurement (the intensity curves of FIGS. 3a and 3b are slightly different), but it is difficult to interpret it in isolation, and the noise levels of CD-SEM prevent satisfactory extraction of information.

Conversely, OCD technology can give information on angle of inclination t (called the SWA, Side Wall Angle) and on the lateral dimension.

In the calibration method according to the invention, two techniques (parametric CD-SEM, firstly, and a reference technique such as AFM, TEM or OCD), are used initially independently of one another. The reference technique obtains information on the topography of the patterns (altitudes, lateral dimensions, etc.). Conversely, CD-SEM essentially provides information relating to the fit parameters which, initially, give no indications as to the topography. CD-SEM can also provide information on the lateral dimensions. The process of calibration then consists in determining a mapping between the parameters of the image modelled by CD-SEM and the geometrical parameters determined by the AFM, TEM or OCD reference technology. After the relationships between the CD-SEM parameters and the geometrical parameters of the reference technology are determined, the technique of modelled CD-SEM characterisation can be used in isolation to determine optimally the lateral dimensions of the objects.

The calibration operation, i.e. the determination of the coefficients of the relationships between the reference measurements and the found CD-SEM mathematical parameters, is undertaken using a set of reference samples characteristic of the objects ultimately to be measured (i.e. a set of calibration samples defining a range of validity will therefore be chosen).

The method of calibration according to the invention therefore consists in taking at least one parameter p for modelling a measurement provided by the CD-SEM technique concerning which it is not known how it relates to one or more physical parameter(s), noted q, determined by the reference characterisation technique.

According to the invention, a search will be made for the function which relates parameter(s) p to physical magnitude(s) q. To accomplish this, a series of n measurements of $q_{exp}$ (n measurements of parameter q) and $p_{exp}$ (n values of model parameter p) is made. The method according to the invention starts with the hypothesis that there exists a mapping function $P_c$ which transforms p into q ($q \leftarrow P_c(p)$), where $P_c$ is characterised by a set of coefficients c (c is comparable to a vector containing a plurality of K coefficients $q_i$, where i varies from 1 to K) which parameterise $P_c$. It will be noted that it has been considered here that mapping function $P_c$ transforms p into q, but the invention also applies equally to a mapping function transforming p into a function g(q), where g is a function for pre-processing of q. The principle of the method of calibration according to the invention then consists in finding the set c such that, for all the measurements, the following distance is minimised: $\|q_{exp} - P_c(p_{exp})\|$ (which can also be written D ($q_{exp}$, $P_c(P_{exp})$)).

The problem of calibration amounts to solving the following equation:

$$c = \text{Argmin}_c \|q_{exp} - P_c(P_{exp})\|$$

This means that c is the estimated value for which distance D between $q_{exp}$ and $P_c(p_{exp})$ is minimal. By way of example, and non-restrictively, the distance could be the least squares distance:

$$D_2(F_1, F_2) = \Sigma(F_1(i,j) - F_2(i,j))^2 \quad \text{(norm L2)}$$

or the least absolute values distance:

$$D_1(F_1, F_2) = \Sigma|F_1(i,j) - F_2(j)| \quad \text{(norm L1)}$$

When coefficients c have been determined from the reference samples, the CD-SEM characterisation technique can then be used alone. Parameters p are measured, and their physical relationship to the profile is determined by the equation:

$$q = P_c(p)$$

The method according to the invention may also have one or more of the characteristics below, considered individually, or in all technically possible combinations:
- the reference characterisation technique is chosen from among one of the following techniques:
  - atomic force microscopy, known as the AFM technique;
  - scatterometry, known as the OCD technique;
  - transmission electron microscopy, TEM;
- the number of measurements is greater than or equal to the number of coefficients to be determined in the mapping function (it will be noted that the value of certain coefficients may be fixed; in this case there is no longer any requirement to determine them);
- by way of example only, the said parameter representative of a measurement provided by the reference characterisation technique is chosen from among the following parameters:
  - width of the pattern;
  - height of the pattern;
  - angle of inclination;
  - measurement representing the upper or lower rounding of the pattern;
  - measurement representative of the shape of the sides of the pattern;
  ...
- by way of example only, the said parameter obtained by modelling a measure provided by the CD-SEM technique is chosen from among the following parameters:
  - position of the diffraction peak(s) of the CD-SEM image;
  - width of the diffraction peak(s) of the CD-SEM image;
  - signal levels (upper and lower signal level, background signal level);
  - expansion of the exponential functions used for modelling;
  - the position of the bottom and/or top of the pattern;
  ...
- by way of example only, the minimised distance is chosen from among one of the following distances:
  - the least squares distance, whether or not weighted;
  - the least absolute values distance;
  - the distance estimated by minimum entropy;
  ...
- according to one particularly advantageous embodiment, the mapping function is a linear function of the different coefficients characterising the said function; this linear model is advantageous since it is simple to apply, as it provides a single solution to the problem of minimisation, particularly by using a distance such as the least squares distance;

one embodiment of this linear model consists in writing the mapping function in the form of a polynomial function of the parameter(s) representing a measurement provided by the CD-SEM technique;

an extension of this linear model consists in writing the mapping function relating parameter q representative of a measurement provided by the reference characterisation technique to parameter(s) p obtained by modelling of measurement provided by the CD-SEM technique according to the following relationship: $q=\Sigma^K_{i=1} f_i(p).c_1$, where the K coefficients $c_1$ designate the plurality of coefficients characterising the mapping function, and functions $f_i(p)$ designate the functions for pre-processing of the parameters p, the mapping function is a non-linear function of the different coefficients characterising the said function;

another extension of this linear model consists in writing the mapping function relating parameter q representative of a measurement provided by the reference characterisation technique to parameter(s) p obtained by modelling of a measurement provided by the CD-SEM technique according to the following relationship: $g(q)=\Sigma^K_{i=1} f_i(p).c_i$, where the K coefficients q designate the plurality of coefficients characterising the mapping function, function g(q) designates a functioning for pre-processing of parameter q, and functions $f_i(p)$ designate functions for pre-processing parameter(s) p;

the said function transforms at least one parameter obtained by modelling a measurement provided by the CD-SEM technique into at least one parameter representative of a measurement provided by a reference characterisation technique (in the previous example function g is therefore the identity function).

Other characteristics and advantages of the invention will become clear from the description which is given of it below, by way of example and non-restrictively, with reference to the appended figures, in which:

FIG. 1 illustrates diagrammatically a secondary electron intensity profile as a function of the profile of a pattern obtained by means of instrumentation of the CD-SEM type;

FIGS. 2a and 2b illustrate a first example of parametric mathematical model of a CD-SEM image;

FIG. 4 illustrates diagrammatically the different steps of method 100 of the invention.

Figure 3A:
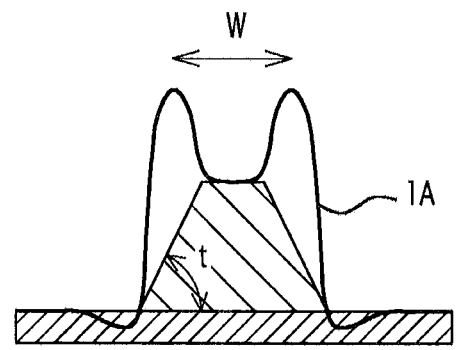
FIG. 3a illustrates diagrammatically the intensity of a CD-SEM profile for an expanding pattern profile.
Figure 3B:
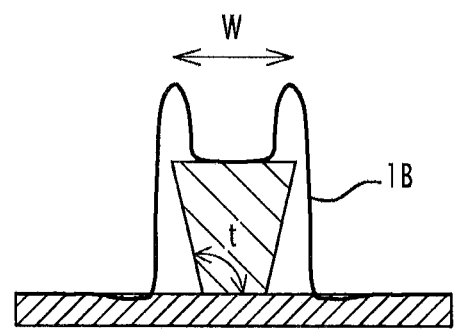
FIG. 3b illustrates diagrammatically the intensity of a CD-SEM profile for a narrowing pattern profile.

Calibration method 100 of the invention seeks to calibrate a CD-SEM technique for the determination of a critical dimension, CD, of any pattern (holes, pins, line, trench, . . . ) belonging to a microelectronic circuit. The material of the pattern can also be any material. This pattern can be, for example, an isolated pattern or a pattern belonging to a network of patterns which are repeated periodically. It may be a pattern obtained after any step (lithography, etching, . . . ) of a manufacturing process.

According to a step 101 of method 100 of the invention, reference samples representative of the field of validity of the calibration which it is desired to implement must be selected.

For example, if it is desired to calibrate the CD-SEM on samples of lines of resin which are 20 nm to 100 nm wide, and which have an inclination angle of 70° to 90°, a number N of samples will be taken which are sufficiently varied to cover the range of variation of both parameters, for example through use of a focus/dose or focus/expo matrix (i.e. The exposure parameters of the lithographic process are varied spatially on the wafer; in one direction the deposited optical power - i.e. the dose - and in the other direction the focus height - i.e. the focus). It will easily be understood that a delicate determination of parameters with a non-robust CD-SEM model and AFM, TEM or OCD reference technique will imply that the number of samples is concentrated in the critical area where accuracy is sought; it will also be possible to oversample over a range in which it is known that accuracy is low (for example on small CDs). It will also easily be understood that the larger the range of validity the greater will be the number of samples.

This type of technique of sample selection comes within the field of Design of Experiments (DOE). Pre-established sampling can, for example, be determined by a regular meshing or by a meshing of the Latin Square type. There are also iterative techniques, such as response functions of the Kriging type, which can indicate, as the technique progresses, the sampling points as a function of the variability of the observed parameters. As an illustration of the present embodiment we shall remain with the case in which there is a DOE technique enabling us to determine correctly the parameters of the model. We shall thus suppose in this case that we have N calibration patterns which sufficiently vary the parameters of interest. It should be noted that in what follows it will be supposed that the number of measurements is greater than or equal to the number of coefficients which must be determined. It should be noted that the number of measurements is not necessarily equal to the number of samples.

Step 101 of selection of the reference samples representative of the field of validity of the calibration is accompanied by a step 102, which consists in determining the mapping function (designated equally below by the terms "law" or "model") relating the parameter(s) obtained by modelling a measurement provided by the CD-SEM technique to the parameter(s) representative of a measurement provided by a reference characterisation technique different from the CD-SEM technique, preferably one of the AFM, TEM or OCD techniques.

As we shall see below, different types of models exist which can be used to relate the CD-SEM mathematical parameters p to the physical parameters q of the reference technique.

According to the invention, at least one parameter p and at least one parameter q will be required, bearing in mind that it is possible to have several parameters p and several parameters q, and that the numbers of parameters p and of parameters q are not necessarily identical. Similarly, parameters q can be representative of measurements derived from one or more reference techniques; for example, certain parameters may be derived from AFM, and certain other parameters may be derived from OCD or TEM.

The term "physical parameter" of the reference technique is understood to mean a parameter representative of the measurement provided by the reference characterisation technique. Thus, as an illustration only, the reference physical parameter can be the width, such as the width of a line of resin on silicon obtained by means of an AFM technique. Without being exhaustive, the reference physical parameters can also be the height of the patterns, the angle of inclination, etc.

Similarly, the term "CD-SEM mathematical parameter" is understood to be unit of data obtained by mathematical modelling of the CD-SEM image.

It will be noted that the examples given below relate to the case of a mathematical model of a CD-SEM image, on the understanding that the invention could also apply to the case of a physical model of the CD-SEM image.

In the examples mentioned below, by way of example only, we have considered only the position parameters of the diffraction peaks in the CD-SEM image, but the invention applies to all types of parameter which may be obtained by means of modelling of the CD-SEM images (width of the peaks, etc.), or even measuring conditions (enlargement of the images, doses, measuring times, etc.).

According to a first embodiment of step 102, it is supposed that the law relating reference parameters q to CD-SEM mathematical parameters p is a polynomial p law.

The analysis of the measurements of the CD-SEM technique and of the AFM/OCD reference technique of a pattern i produces the row vector of parameter $p_i$, and $q_i$. In this case the CD-SEM and AFM/OCD reference techniques give for each sample parameters m and n (respective lengths of row vectors $p_{i:}$ and $q_{i:}$). If it is supposed, for example, that these quantities are related by a polynomial of order 2 with cross-terms, this therefore gives, with m=2 (i.e. two CD-SEM parameters $p_{i1}$ and $p_{i2}$ for pattern i) and, considering first term $q_{i1}$ of row vector $q_i$:

$$q_{i,1} \simeq c_0 + p_{i1}c_1 + p_{i2}c_2 + p_{i1}^2 c_3 + p_{i2}^2 c_4 + p_{i1}p_{i2}c_5$$

$$\simeq (1 \quad p_{i1} \quad p_{i2} \quad p_{i1}^2 \quad p_{i2}^2 \quad p_{i1}p_{i2}) \begin{pmatrix} c_0 \\ c_1 \\ c_2 \\ c_3 \\ c_4 \\ c_5 \end{pmatrix}$$

with K (in this case K=5) coefficients $c_i$ characterising the mapping function Thus, by making N measurements (step 103), the following matrix relationship is obtained:

$$q_{:,1} \simeq \begin{pmatrix} 1 & p_{11} & p_{12} & p_{11}^2 & p_{12}^2 & p_{11}p_{12} \\ 1 & p_{21} & p_{22} & p_{21}^2 & p_{22}^2 & p_{21}p_{22} \\ \cdots \\ 1 & p_{i1} & p_{i2} & p_{i1}^2 & p_{i2}^2 & p_{i1}p_{i2} \\ \cdots \\ 1 & p_{N1} & p_{N2} & p_{N1}^2 & p_{N2}^2 & p_{N1}p_{N2} \end{pmatrix} \begin{pmatrix} c_0 \\ c_1 \\ c_2 \\ c_3 \\ c_4 \\ c_5 \end{pmatrix} = P_1 c$$

Consistently with the previously used notation, this therefore gives $P_c = P_1 \times c$, where function $P_c$ is the mapping function which transforms p into q ($q \leftarrow P_c(p)$). It is observed in this case that the chosen model is a linear model as a function of coefficients $c_i$ (vector c), such that there is a matrix relationship between the vector of parameters q and vector c of coefficients $c_i$, and that the said matrix depends solely on parameters p and not on coefficients $c_i$.

According to step 104, the coefficients of parameters vector c are determined by minimising the distance:

$$c = \operatorname{Argmin}_c \| q_{:,1} - P_1 c \|$$

If it is desired to minimise according to least squares norm L2, the solution is given directly by the following relationship:

$$c = P_1 \dagger q_{:,1}$$

where $P_1\dagger$ is the pseudo-inverse matrix of $P_1$.

When the distance is not L2 (L1 for example), or alternatively if constraints are added to the system (constraints at intervals to which the parameters must belong, linear or non-linear constraints of the parameters, addition of penalty functions, etc.), other algorithms known to those skilled in the art can be used for the resolution of the linear system.

According to step 105, when vector c has been determined after minimisation, knowledge of function $P_c$ to which this set of coefficients c is applied enables the parametric CD-SEM method to be used alone (i.e. without the assistance of another characterisation technique), both for R&D and for production, across the full range of validity: in other words, mathematical CD-SEM parameters p are measured, the line of $P_1$ is then formed, and physical quantity of interest $q_1$ is found using the simple formula $q_1 = P_1 c$.

As was mentioned above, the mathematical CD-SEM parameters can be of different types. Let us take, for example, the CD-SEM model of a rectangle (illustrated in FIG. 5), written with parameters $x_1$, $x_2$, a, b, $w, y_{()}$, which represent respectively the two abscissae of the secondary electron intensity peaks, the lower and upper signal levels, the expansion of the exponential functions, and the level of the background signal.

The profile can then be modelled, for example, by the function y(x), which is broken down into three sub-functions, depending on whether x is less than $x_1$, between $x_1$ and $x_2$ or greater than $x_2$:

$$y(x) = y_0 + (a+b)\exp(-(x-x_1)^2/2/w^2) \text{ si } x < x_1$$

$$= y_0 + a + b\exp(-(x-x_1)^2/2/w^2) +$$
$$\quad b\exp(-(x-x_2)^2/2/w^2) \text{ si } x \in [x_1, x_2]$$

$$= y_0 + (a+b)\exp(-(x-x_2)^2/2/w^2) \text{ si } x > x_2$$

The mathematical parameters of the model are therefore, in this case, (making $y_0 = 0$):

$x_1, x_2, a, b, w.$

With reference to the document "CD characterization of nanostructures in SEM metrology" (C. G. Frase, E. Buhr, and K. Dirscherl, Meas. Sci. Technol., vol. 18, no 2, p. 510, February. 2007) cited previously in reference to function M(x) illustrated in FIG. 2b, the CD-SEM mathematical parameters can be: $x_1, x_2, x_3, x_4, x_5, S_0, S_1, X_2, S_3, t_0, t_1, t_2, t_3, t_4, t_5, A, B, C, D.$ In this latter case, bearing in mind the number of parameters which must be determined, the number of samples must be higher and/or constraints relating to the parameters must be imposed.

One possibility to reduce the number of parameters can consist in:

given: $u_1 = \dfrac{x_2 + x_1}{2}, u_1 = \dfrac{x_5 + x_4}{2},$ imposing $x_3 = (u_1 + u_2)/2$ $S_1 = S_3,$ $t = t_i V_i.$ The mathematical parameters to be calibrated then become:

$u_1, u_2, S_0, S_1, S_2, t, A, B, C, D.$

Without altering the general character of the linear approach (i.e. there is always a linear system which can be written according to the matrix relationship: q=P×c), according to step 102, it can be observed that the formation of matrix $P_1$ in order to determine physical parameter $q_1$ from parameters p is arbitrary. Indeed, the CD-SEM parameters p can equally be pre-processed, in order to form matrix $P_1$; in other words, it is not necessary to use parameters p directly. The system shown above can then be written in the following form:

$$f_q(q_{:,1}) \simeq \begin{pmatrix} f_0(p_{1:}) & f_1(p_{1:}) & f_2(p_{1:}) & f_3(p_{1:}) & f_4(p_{1:}) & f_5(p_{1:}) \\ f_0(p_{2:}) & f_1(p_{2:}) & f_2(p_{2:}) & f_3(p_{2:}) & f_4(p_{2:}) & f_5(p_{2:}) \\ \cdots \\ f_0(p_{i:}) & f_1(p_{i:}) & f_2(p_{i:}) & f_3(p_{i:}) & f_4(p_{i:}) & f_5(p_{i:}) \\ \cdots \\ f_0(p_{N:}) & f_1(p_{N:}) & f_2(p_{N:}) & f_3(p_{N:}) & f_4(p_{N:}) & f_5(p_{N:}) \end{pmatrix} \begin{pmatrix} c_0 \\ c_1 \\ c_2 \\ c_3 \\ c_4 \\ c_5 \end{pmatrix} = P_1 c$$

(relationship 1)

where the K functions $f_i(p)$ (where K is equal to the number of coefficients $c_i$ characterising the mapping function) are pre-processing functions, which the user can choose according to the specific characteristics of the problem. In the above example a pre-processing function $f_q$ is also applied to vector q (i.e. both parameters p and q can be pre-processed). In this case, in order to obtain q after this, function fq must be reversed; in other words, we shall obtain $q = f_q^{-1}(f_q(q))$.

In what follows we shall illustrate the case of the extension of the linear model using simple pre-processing functions.

Parameter q is, in this case, width w of resin lines on silicon obtained by an AFM measurement which is the reference technique in this case. An analysis of the 14 quantities (N=14) gives a vector $q_{:,1}$ containing 14 line widths $w_1 \ldots _{14} = q_{:,1}$. The quantities of the vector are given in nm in the second column of table 1 below.

TABLE 1

| Image n° | w obtained by AFM (nm) | Delta = x2 − x1 (nm) | CDSEM (80%) |
|---|---|---|---|
| 1 | 32.84 | 23.09 | 32.92 |
| 2 | 43.15 | 29.45 | 38.88 |
| 3 | 52.33 | 37.45 | 47.40 |
| 4 | 89.02 | 73.53 | 81.86 |
| 5 | 100.65 | 86.11 | 94.07 |
| 6 | 111.66 | 95.34 | 105.90 |
| 7 | 121.54 | 105.74 | 114.63 |
| 8 | 129.85 | 115.43 | 123.76 |
| 9 | 139.33 | 123.99 | 133.81 |
| 10 | 147.30 | 132.52 | 142.23 |
| 11 | 157.10 | 143.87 | 152.14 |
| 12 | 166.85 | 153.36 | 162.53 |
| 13 | 176.56 | 164.45 | 173.65 |
| 14 | 279.84 | 267.50 | 275.82 |

Figure 5:
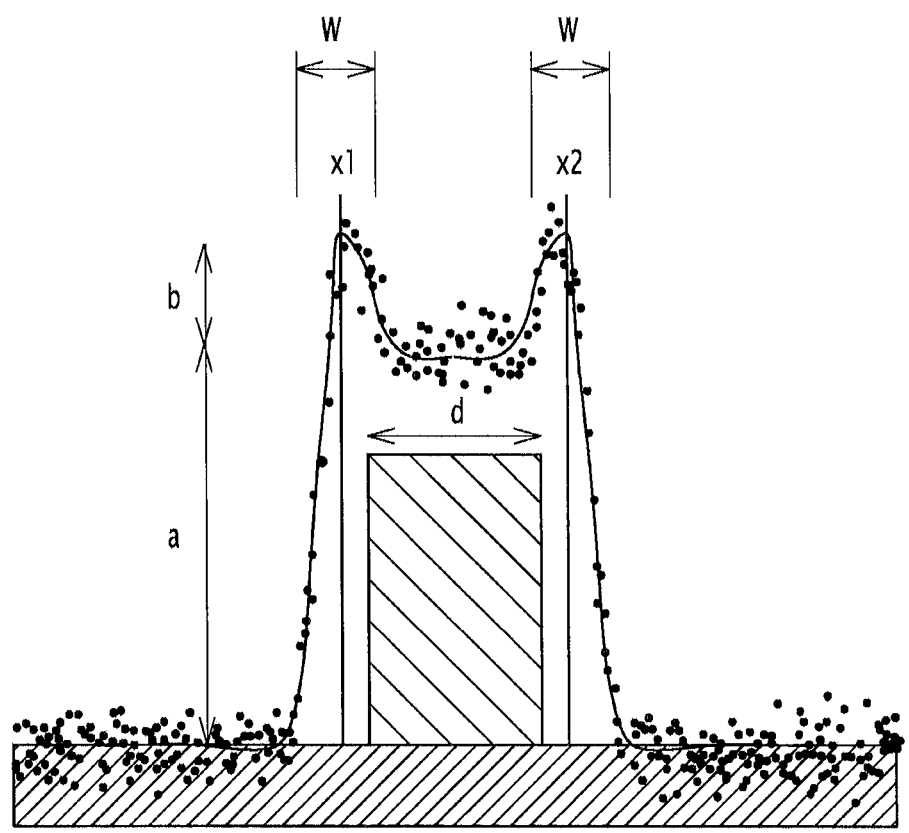
FIG. 5 illustrates a second example of mathematical modelling
of a CD-SEM image.
Figure 6:
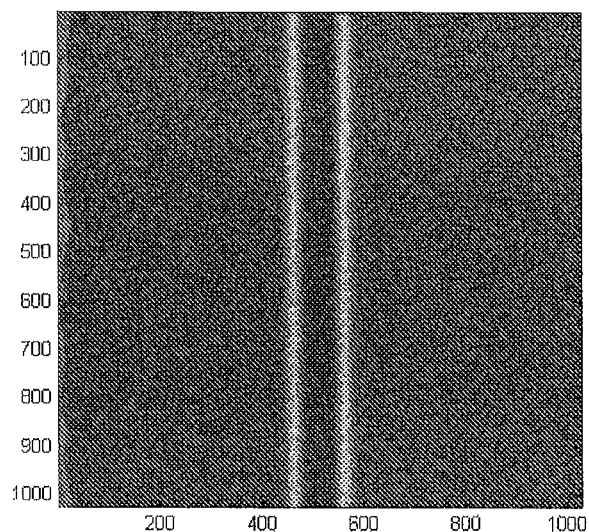
FIG. 6 is a CD-SEM image of a line of resin on silicon.
Figure 7:
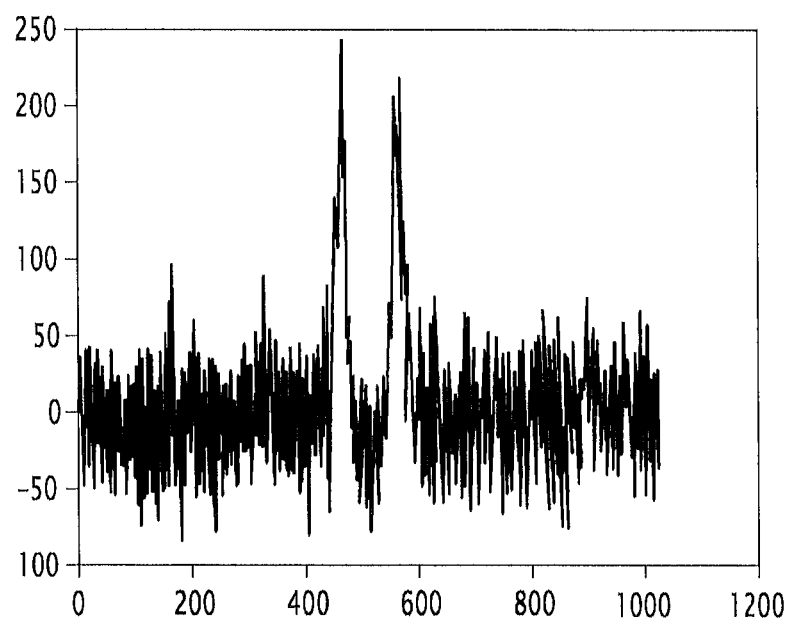
FIG. 7 represents two diffraction peaks of the secondary electrons at the edges of the line imaged by CD-SEM represented in FIG. 6.

Simultaneously with the measurements of the reference technique, CD-SEM images are produced and a parametric analysis of the said image is made: the model used is, for example, the model illustrated in FIG. 5 (approximation of the intensity profile by the function y(x) described in detail above).

Figure 4:
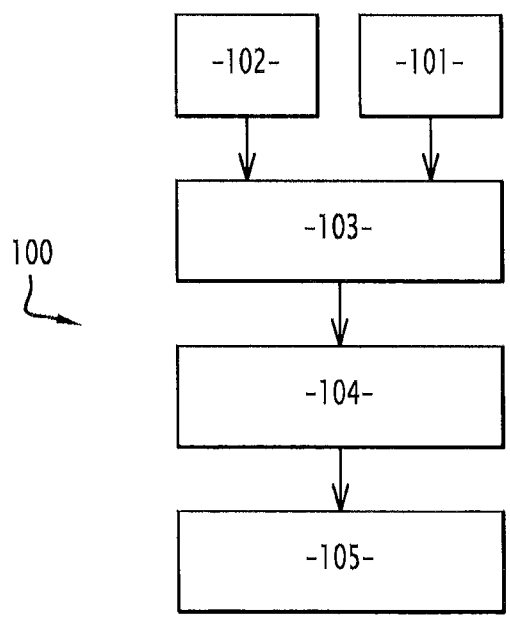
FIG. 4 represents the different steps of the method of the invention.

By constraining parameters a, b and w and to simplify the explanation of the method of the invention, we consider here only two mathematical parameters, $x_1$ and $x_2$, for the images obtained by the CD-SEM technique corresponding to the positions of the two diffraction peaks of the secondary electrons at the edges of the line. These peaks, which are illustrated in FIG. 5 (and which correspond to the CD-SEM image of FIG. 4) are noted for the image: i: $x_{i,1} = p_{i,1}$ and $x_{i,2} = p_{i,2}$ ((it is supposed that $x_{i,2} > x_{i,1}$). At this point it is not known how the positions of the peaks obtained with CD-SEM relate to the widths of the lines obtained by the AFM reference technique. The third column of table 1 shows the value of difference $p_{i,2} - p_{i,1}$ (i.e. $x_{i,2} - x_{i,1}$) for each measurement i. If the distance between two peaks was equal to the value given by AFM, we would have $q_{i,1} = -p_{i,1} + p_{i,2}$. By comparing the values of the second column and the third column it is observed that this is absolutely not the case. The average quadratic error compared to AFM is in this case equal to 14.1 nm.

As a comparison, the last column of table 1 also contains the measurement of the critical dimension obtained by the non-calibrated CD-SEM analysis technique, i.e. an analysis by studying the contours of the peaks taken with thresholding of 80% of the height of the peak. The average quadratic error compared to the AFM measurement is 5.2 nm: this quadratic error is therefore less than the quadratic error obtained in the case of the model of the peak-to-peak distance, but is still too high; one of the goals of the method of calibration of the invention is to reduce this quadratic error.

For physical reasons it may be supposed initially that the following applies: $q_{i,1} = c_0 + c_1 f(p_{i,1}, p_{i,2})$, where $f(x_1, x_2) = x_2 - x_1$; by using the previous notation of relationship 1 it is possible to write:

$$f_0(p_{i1}) = f_0(X_1, X_2) = 1 \text{ and } f_1(p_{i1}) = f_1(X_1, X_2) = X_2 - X_1$$

The following will subsequently be noted: $p_{i,2} - p_{i,1} = x_{i,1} - x_{i,1} = \Delta_i$.

The method of the invention seeks to determine coefficients $c_1$ (in this case two coefficients $c_o$ and $c_1$ characterising the mapping function), and then to use these coefficients when implementing the CD-SEM technique in production. The formation of matrix Pi derived from the analysis of the 14 images gives a matrix of 14 lines (i.e. the number of measurements) and 2 columns (i.e. the number of coefficients). The pseudo-inverse matrix is determined, and the following is obtained experimentally: $c_0 = 14.33$ nm and $c_1 = 0.997$. The average quadratic error between the model obtained by the method of the invention and the reference measurement (in this case the AFM technique) is 1.68 nm. An average quadratic error is therefore obtained which is far lower than the average quadratic error between the CD-SEM model with thresholding of 80% of the height of the peak and the AFM technique.

According to a first variant, additional polynomial terms can be included by adding two additional coefficients $c_2$ and $c_3$:

$$q_{i,1} = c_0 + c_1 \Delta_i^2 + c_3 \Delta_i^3$$

Using the previous notations of relationship 1, it is possible to write:

$f_0(p_{i1})=f_0(X_i, X_2)=1$ $f_1(p_{i1})=f_1(X_1, X_2)=X_2-X_1$ $f_2(p_{i1})=f_1(X_1, X_2)=X_2-X_1)^2$ $f_3(p_{i1i})=f_1(X_1, X_2)-(X_2-X_1)^3$

Matrix P therefore has 14 lines and 4 columns. The average quadratic error between the model obtained by the method of the invention and the reference measurement (in this case AFM) is in this case 0.75 nm, and is again therefore substantially smaller According to a second variant, the following model may be supposed:

$$q_{i,1} = c_0 + c_1 \Delta_i + \frac{c_2}{\Delta_i} + \frac{c_3}{\Delta_i^2}$$

Using the previous notations of relationship 1, it is possible to write:

$f_0(p_{i1})=f_0(X_1, X_2)=1$ $f_1(p_{i1})=f_1(X_1, X_2)=X_2-X_2)=1$ $f_2(p_{i1})=f_1(X_2-X_1)$ $f_3(p_{i1})=f_1(x_1, X_2)=1/(x_2-X_1)^2$

As with the previous case, matrix P has 14 lines and 4 columns. The average quadratic error between the model obtained by the method of the invention and the reference measurement (in this case AFM) is in this case 0.73 nm, and is once again smaller than the first variant.

Through these models the importance and influence of the choice of the model to which the measurements will subsequently be applied will be understood.

According to another embodiment of method 100 of the invention, step 102 may consist of determining a mapping function not based on a linear model; in other words, there is a matrix relationship between the vector of parameters q and vector c of coefficients with a matrix which would depend only on parameters p, and not on coefficients $c_i$.

If we return to the initial formation, the calibration problem amounts to resolving the following equation $c=\text{Argmin}_c\|q_{exp}-P_c(p_{exp})\|$ i.e. that c is the estimated value for which distance D between $q_{exp}$ and $P_c(p_{exp})$ is minimal.

The problem considered in terms of its general character still has no single solution, due to the non-linearity of $P_c$. Several strategies known to those skilled in the art can be envisaged, such as a global optimisation, or selection of convex domains (in which the solution is unique), and a local optimisation in the convex domain.

As an example, the following non-linear model may be used:

$$q_{i,1} = c_0 + c_1 \Delta_i + c_2 \arctan\left(\frac{\Delta_i}{c_3}\right)$$

Non-restrictively, after being calibrated by the method of the invention CD-SEM technology can, for example, be used for techniques to improve OPC (Optical Proximity Correction) models. For this application, reliable information concerning the dimensions of the objects is required in order to develop the behaviour models of the lithography tools.

The invention claimed is:

1. A method of calibrating a CD-SEM technique of characterisation by scanning electron microscopy in order to determine a critical dimension, said method comprising:
   determining a mapping function transforming at least one parameter obtained by modelling a measurement provided by the CD-SEM technique into a function of at least one parameter representative of a measurement provided by a reference characterisation technique different from the CD-SEM technique, wherein the mapping function is characterised by a plurality of coefficients;
   making measurements on a plurality of physical patterns chosen to cover a field of validity desired for the calibration, wherein the measurements on the plurality of physical patterns are made using both the CD-SEM technique of characterisation by scanning electron microscopy requiring calibration and the reference characterisation technique;
   determining, from the measurements, a set of coefficients of the mapping function minimising a distance between the functions of the parameters measured by the reference characterisation technique and applying the mapping function to the parameters obtained by modelling the measurements provided by the CD-SEM technique;
   using the set of coefficients when using the calibrated CD-SEM technique.

2. The method according to claim 1, wherein said reference characterisation technique is chosen from among one of the following techniques:
   atomic force microscopy;
   scatterometry;
   transmission electron microscopy.

3. The method according to claim 1, wherein the number of measurements is greater than or equal to the number of coefficients to be determined in the mapping function.

4. The method according to claim 1, wherein the mapping function is a linear function of the different coefficients characterising the function.

5. The method according to claim 4, wherein the mapping function relating parameter q representative of a measurement provided by the reference characterisation technique to parameter(s) p obtained by modelling of measurement provided by the CD-SEM technique is written as follows: $q=\Sigma^K_{i=1}f_i(p).c_i$, where the K coefficients $c_i$ designate the plurality of coefficients characterising the mapping function, and functions $f_i(p)$ designate functions for pre-processing parameter(s) p.

6. The method according to claim 5, wherein the mapping function is a polynomial function of the parameter(s) obtained by modelling a measurement provided by the CD-SEM technique.

7. The method according to claim 4, wherein the mapping function relating parameter q representative of a measurement provided by the reference characterisation technique to parameter(s) p obtained by modelling of measurement provided by the CD-SEM technique is written as follows: $g(q)=\Sigma^K_{i=1}f_i(p).c_i$, where the K coefficients $c_i$ designate the plurality of coefficients characterising the mapping function, function g(q) designates a functioning for pre-processing of parameter q, and functions $f_i(p)$ designate functions for pre-processing parameter(s) p.

8. The method according to claim 1, wherein the mapping function is a non-linear function of the different coefficients characterising the function.

9. The method according to claim 1, wherein the mapping function transforms at least one parameter obtained by modelling of a measurement provided by the CD-SEM technique into at least one parameter representing a measurement provided by a reference characterisation technique.

* * * * *